United States Patent
Reicher et al.

(10) Patent No.: US 9,042,617 B1
(45) Date of Patent: May 26, 2015

(54) RULES-BASED APPROACH TO RENDERING MEDICAL IMAGING DATA

(71) Applicant: DR Systems, Inc., San Diego, CA (US)

(72) Inventors: Murray A. Reicher, Rancho Santa Fe, CA (US); Evan K. Fram, Paradise Valley, AZ (US)

(73) Assignee: DR SYSTEMS, INC., San Diego, CA (US)

( * ) Notice: Subject to any disclaimer, the term of this patent is extended or adjusted under 35 U.S.C. 154(b) by 0 days.

(21) Appl. No.: 14/179,328

(22) Filed: Feb. 12, 2014

Related U.S. Application Data

(63) Continuation of application No. 12/891,543, filed on Sep. 27, 2010, now Pat. No. 8,712,120.

(60) Provisional application No. 61/246,479, filed on Sep. 28, 2009.

(51) Int. Cl.
  *G06K 9/00* (2006.01)
  *H04L 29/08* (2006.01)

(52) U.S. Cl.
  CPC ............ *H04L 67/02* (2013.01); *G06F 2101/00* (2013.01)

(58) Field of Classification Search
  None
  See application file for complete search history.

(56) References Cited

U.S. PATENT DOCUMENTS

| | | | |
|---|---|---|---|
| 4,672,683 A | 6/1987 | Matsueda | |
| 5,123,056 A | 6/1992 | Wilson | |
| 5,179,651 A | 1/1993 | Taaffe et al. | |
| 5,431,161 A | 7/1995 | Ryals et al. | |
| 5,452,416 A | 9/1995 | Hilton et al. | |
| 5,542,003 A | 7/1996 | Wofford | |
| 5,734,915 A | 3/1998 | Roewer | |
| 5,740,267 A | 4/1998 | Echerer et al. | |
| 5,779,634 A | 7/1998 | Ema et al. | |
| 5,852,646 A | 12/1998 | Klotz et al. | |
| 5,926,568 A | 7/1999 | Chaney et al. | |
| 5,954,650 A | 9/1999 | Saito et al. | |
| 5,976,088 A | 11/1999 | Urbano et al. | |
| 5,986,662 A | 11/1999 | Argiro et al. | |
| 5,987,345 A | 11/1999 | Engelmann et al. | |
| 5,995,644 A | 11/1999 | Lai et al. | |
| 6,115,486 A | 9/2000 | Cantoni | |
| 6,128,002 A | 10/2000 | Leiper | |
| 6,151,581 A | 11/2000 | Kraftson et al. | |
| 6,175,643 B1 | 1/2001 | Lai et al. | |
| 6,177,937 B1 | 1/2001 | Stockham et al. | |
| 6,185,320 B1 | 2/2001 | Bick et al. | |

(Continued)

FOREIGN PATENT DOCUMENTS

WO   WO 2007/131157   11/2007

OTHER PUBLICATIONS

US 7,801,341, Sep. 2010, Fram et al., (withdrawn).

(Continued)

*Primary Examiner* — Tahmina Ansari
(74) *Attorney, Agent, or Firm* — Knobbe, Martens, Olson & Bear LLP

(57) ABSTRACT

Systems and methods that allow transfer criteria to be defined based on one or more of several attributes, such as a particular user, site, or device, as well as whether individual images and/or image series are classified as thin slices, and applied to medical images in order to determine which images are downloaded, viewed, stored, and/or any number of other actions that might be performed with respect to particular images.

22 Claims, 7 Drawing Sheets

(56) References Cited

U.S. PATENT DOCUMENTS

| | | |
|---|---|---|
| 6,243,095 B1 | 6/2001 | Shile et al. |
| 6,269,379 B1 | 7/2001 | Hiyama et al. |
| 6,304,667 B1 | 10/2001 | Reitano |
| 6,347,329 B1 | 2/2002 | Evans |
| 6,351,547 B1 | 2/2002 | Johnson et al. |
| 6,383,135 B1 | 5/2002 | Chikovani et al. |
| 6,388,687 B1 | 5/2002 | Brackett et al. |
| 6,424,996 B1 | 7/2002 | Killcommons et al. |
| 6,438,533 B1 | 8/2002 | Spackman et al. |
| 6,463,169 B1 | 10/2002 | Ino et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,618,060 B1 | 9/2003 | Brackett |
| 6,630,937 B2 | 10/2003 | Kallergi et al. |
| 6,678,764 B2 | 1/2004 | Parvulescu et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,093 B2 | 11/2004 | de la Huerga |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 | 5/2007 | Belykh et al. |
| 7,224,852 B2 | 5/2007 | Lipton et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,505,782 B2 | 3/2009 | Chu |
| 7,526,114 B2 | 4/2009 | Seul et al. |
| 7,526,132 B2 | 4/2009 | Koenig |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,656,543 B2 | 2/2010 | Atkins |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,094,901 B1 | 1/2012 | Reicher et al. |
| 8,217,966 B2 | 7/2012 | Fram et al. |
| 8,244,014 B2 | 8/2012 | Reicher et al. |
| 8,292,811 B2 | 10/2012 | Relkuntwar et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,879,807 B2 | 11/2014 | Fram et al. |
| 8,913,808 B2 | 12/2014 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0073429 A1 | 6/2002 | Beane et al. |
| 2002/0090124 A1 | 7/2002 | Soubelet et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0180883 A1 | 12/2002 | Tomizawa et al. |
| 2003/0005464 A1 | 1/2003 | Gropper et al. |
| 2003/0016850 A1 | 1/2003 | Kaufman et al. |
| 2003/0028402 A1 | 2/2003 | Ulrich et al. |
| 2003/0037054 A1 | 2/2003 | Dutta et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0140141 A1 | 7/2003 | Mullen et al. |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105574 A1 | 6/2004 | Pfaff |
| 2004/0114714 A1 | 6/2004 | Minyard et al. |
| 2004/0141661 A1* | 7/2004 | Hanna et al. ............... 382/305 |
| 2004/0143582 A1 | 7/2004 | Vu |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |

(56) References Cited

U.S. PATENT DOCUMENTS

| | | |
|---|---|---|
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1* | 1/2005 | Kushalnagar et al. .......... 705/59 |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0095426 A1 | 5/2006 | Takachio et al. |
| 2006/0111941 A1 | 5/2006 | Blom |
| 2006/0171574 A1 | 8/2006 | DelMonego et al. |
| 2006/0181548 A1 | 8/2006 | Hafey |
| 2006/0230072 A1 | 10/2006 | Partovi et al. |
| 2006/0241979 A1* | 10/2006 | Sato et al. .................... 705/3 |
| 2006/0277075 A1 | 12/2006 | Salwan |
| 2006/0282408 A1 | 12/2006 | Wisely et al. |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109402 A1 | 5/2007 | Niwa |
| 2007/0124541 A1 | 5/2007 | Lang et al. |
| 2007/0159962 A1 | 7/2007 | Mathavu et al. |
| 2007/0162308 A1 | 7/2007 | Peters |
| 2007/0174079 A1 | 7/2007 | Kraus |
| 2007/0192140 A1 | 8/2007 | Gropper |
| 2007/0239481 A1 | 10/2007 | DiSilvestro et al. |
| 2008/0016111 A1 | 1/2008 | Keen |
| 2008/0059245 A1 | 3/2008 | Sakaida et al. |
| 2008/0100612 A1 | 5/2008 | Dastmalchi et al. |
| 2008/0103828 A1 | 5/2008 | Squilla et al. |
| 2008/0125846 A1 | 5/2008 | Battle et al. |
| 2008/0126982 A1 | 5/2008 | Sadikali et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2009/0028410 A1 | 1/2009 | Shimazaki |
| 2009/0080719 A1 | 3/2009 | Watt |
| 2009/0123052 A1 | 5/2009 | Ruth et al. |
| 2009/0129643 A1* | 5/2009 | Natanzon et al. ............. 382/128 |
| 2009/0132586 A1 | 5/2009 | Napora et al. |
| 2009/0150481 A1* | 6/2009 | Garcia et al. .................. 709/203 |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2010/0053353 A1 | 3/2010 | Hunter et al. |
| 2010/0198608 A1 | 8/2010 | Kaboff et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram |
| 2011/0110572 A1 | 5/2011 | Guehring et al. |
| 2011/0316873 A1 | 12/2011 | Reicher |
| 2012/0130729 A1 | 5/2012 | Raizada et al. |
| 2012/0163684 A1 | 6/2012 | Natanzon et al. |
| 2012/0194540 A1 | 8/2012 | Reicher |
| 2013/0083023 A1 | 4/2013 | Fram |
| 2013/0159019 A1 | 6/2013 | Reicher |
| 2013/0169661 A1 | 7/2013 | Reicher |

OTHER PUBLICATIONS

US 8,208,705, Jun. 2012, Reicher et al., (withdrawn).

Crowley, Rebecca et al., Development of Visual Diagnostic Expertise in Pathology: an Information-processing Study, Jan. 2003, Journal of the American medical Informatics Association, vol. 10, No. 1, pp. 39-51.

Non-Final Office Action dated Aug. 28, 2007 in U.S. Appl. No. 11/179,384.

Final Office Action dated Jun. 26, 2008 in U.S. Appl. No. 11/179,384.

Non-Final Office Action dated Dec. 29, 2008 in U.S. Appl. No. 11/179,384.

Final Office Action dated Jul. 24, 2009, in U.S. Appl. No. 11/179,384.

Notice of Allowance dated Nov. 3, 2009, in U.S. Appl. No. 11/179,384.

Non-Final Office Action dated Aug. 18, 2010 in U.S. Appl. No. 12/702,976.

Interview Summary dated Dec. 1, 2010, in U.S. Appl. No. 12/702,976.

Final Office Action dated Feb. 17, 2011 in U.S. Appl. No. 12/702,976.

Interview Summary dated May 31, 2011 in U.S. Appl. No. 12/702,976.

Notice of Allowance dated Jul. 20, 2011, in U.S. Appl. No. 12/702,976.

Office Action dated Dec. 1, 2011, in U.S. Appl. No. 13/228,349.

Notice of Allowance dated Feb. 6, 2012, in U.S. Appl. No. 13/228,349.

Notice of Allowance dated Jul. 20, 2012, in U.S. Appl. No. 13/228,349.

Office Action dated Dec. 11, 2013, in U.S. Appl. No. 13/477,853.

Interview Summary dated May 14, 2010, in U.S. Appl. No. 11/268,261.

Notice of Allowance dated May 17, 2010, in U.S. Appl. No. 11/268,261.

Supplemental Notice of Allowance dated Aug. 6, 2010, in U.S. Appl. No. 11/268,261.

Notice of Allowance dated Oct. 8, 2010, in U.S. Appl. No. 11/268,261.

Notice of Allowance dated Dec. 3, 2010, in U.S. Appl. No. 11/268,261.

Notice of Allowance dated Jan. 6, 2011, in U.S. Appl. No. 11/268,261.

Office Action dated May 16, 2011, in U.S. Appl. No. 12/857,915.

Interview Summary dated Sep. 6, 2011, in U.S. Appl. No. 12/857,915.

Final Office Action dated Dec. 15, 2011, in U.S. Appl. No. 12/857,915.

Office Action dated Jun. 12, 2012, in U.S. Appl. No. 12/857,915.

Office Action dated Aug. 23, 2013, in U.S. Appl. No. 12/857,915.

Interview Summary dated Feb. 4, 2014, in U.S. Appl. No. 12/857,915.

Non-Final Office Action dated May 13, 2009, in U.S. Appl. No. 11/265,979.

Final Office Action dated Dec. 22, 2009 in U.S. Appl. No. 11/265,979.

Non-Final Office Action dated Jul. 8, 2010 in U.S. Appl. No. 11/265,979.

Interview Summary dated Mar. 4, 2010 in U.S. Appl. No. 11/265,979.

Interview Summary dated Nov. 16, 2010 in U.S. Appl. No. 11/265,979.

Final Office Action dated Dec. 23, 2010 in U.S. Appl. No. 11/265,979.

(56) References Cited

OTHER PUBLICATIONS

Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Mendelson, et al., "Informatics in Radiology—Image Exchange: IHE and the Evolution of Image Sharing," RadioGraphics, Nov.-Dec. 2008, vol. 28, No. 7.
Erickson, et al.: "Image Registration Improves Confidence and Accuracy of Image Interpretation," Special Issue-Imaging Informatics, Cancer Informatics 2007: 1 19-24.
Erickson, et al.: "Effect of Automated Image Registration on Radiologist Interpretation," Journal of Digital Imaging, vol. 20, No. 2 Jun. 2007; pp. 105-113.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Issue Notice dated Sep. 1, 2010, in U.S. Appl. No. 11/268,261.
Notice of Allowance dated Jul. 3, 2014, in U.S. Appl. No. 12/857,915.
"Corrected" Notice of Allowance dated Aug. 15, 2014, in U.S. Appl. No. 12/857,915.
Notice of Allowance dated Dec. 1, 2010 in U.S. Appl. No. 11/268,262.
Office Action, dated Mar. 13, 2014 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Office Action dated Sep. 11, 2014 in U.S. Appl. No. 14/179,328.
Schellingerhout, Dawid, MD, et al.: "Coregistration of Head CT Comparison Studies: Assessment of Clinical Utility," Acad Radiol 2003; 10:242-248.
Office Action dated Mar. 3, 2015 in U.S. Appl. No. 14/095,123.

(56) References Cited

OTHER PUBLICATIONS

Interview Summary, dated Mar. 2, 2015 in U.S. Appl. No. 14/298,806.
Interview Summary, dated Mar. 4, 2015 in U.S. Appl. No. 11/942,687.
Final Office Action dated Apr. 1, 2015 in U.S. Appl. No. 14/043,165.
Office Action dated Mar. 17, 2015 in U.S. Appl. No. 13/768,765.
Notice of Allowance dated Mar. 19, 2015, in U.S. Appl. No. 13/572,397.
Notice of Allowance, dated Mar. 3, 2015 in U.S. Appl. No. 13/572,547.
Corrected Notice of Allowability, dated Apr. 10, 2015 in U.S. Appl. No. 13/572,547.
Final Office Action dated Jan. 28, 2015 in U.S. Appl. No. 13/572,552.
U.S. Appl. No. 12/437,522, filed May 7, 2009, Fram.
U.S. Appl. No. 13/572,397, filed Aug. 10, 2012, Reicher.
U.S. Appl. No. 13/572,547, filed Aug. 10, 2012, Reicher.
U.S. Appl. No. 13/572,552, filed Aug. 10, 2012, Reicher.
Interview Summary dated Jan. 25, 2010, in U.S. Appl. No. 11/268,261.
Office Action, dated Dec. 29, 2014 in U.S. Appl. No. 14/298,806.
Office Action dated Jun. 27, 2014 in U.S. Appl. No. 13/572,397.
Final Office Action dated Jan. 13, 2015 in U.S. Appl. No. 13/572,397.
Office Action dated Aug. 6, 2014 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Agfa HealthCare, color brochure "IMPAX 6: Digital Image and Information Management," ©2012 Agfa HealthCare N. V. Downloaded from http://www.agfahealthcare.com/global/en/he/library/libraryopen?ID=32882925. Accessed on Feb. 9, 2015.
Agfa HealthCare, IMPAX 6.5 Datasheet (US)2012. ©2012 Agfa HealthCare N. V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
Aspyra's Imaging Solutions, 3 page color print out. Accessed at http://www.aspyra.com/imaging-solutions. Accessed on Feb. 9, 2015.
Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
Candelis, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Jun. 2012). © Carestream Health, Inc., 2012. Downloaded from http://www.carestream.com/cardioPACS_brochure M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BRO80809AUS), © 2009 iCRco.ClarityPACS. Downloaded from http://www.claritypacs.com/pdfs/ISeeFuture_26_Web.pdf. Accessed on Feb. 9, 2015.
imageanalysis, dynamika, 2 page color brochure. Downloaded from http://www.imageanalysis.org.uk/what-we-do. Accessed on Feb. 9, 2015.
imageanalysis, MRI Software, in 5 page printout. Accessed at http://www.imageanalysis.org.uk/mri-software. Accessed on Feb. 9, 2015.
IMSI, Integrated Modular Systems, Inc., Hosted/Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com,

(56) References Cited

OTHER PUBLICATIONS

May 2012, pp. 24-27. Downloaded from http://www.merge.com/MergeHealthcare/media/company/In%20The%20News/merge-pacs-comparison.pdf. Accessed on Feb. 9, 2015.
Lumedx CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
Lumedx Cardiovascular Information System, CardioPACS, one page in color printout. Accessed at http://www.lumedx.com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
Novarad Enterprise Imaging Solutions, NOVAPACS, 2 page (color) printout. Accessed at http://ww1.novarad.net/novapacs. Accessed on Feb. 9, 2015.
PACPLUS, PACPLUS Server, 1 page (color) printout. Accessed at http://www.pacsplus.com/01_products/products_01.html. Accessed on Feb. 9, 2015.
PACPLUS, PACPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499- 516.
Tahmoush, D. and Samet, H., A New Database for Medical Images and Information, 2007, Medical Imaging 2007; PACS and Imaging Informatics, vol. 6516. pp. 1-9.

\* cited by examiner

*Sample categories of properties/attributes on which rules of transer criteria might be based*

| |
|---|
| Slice Thickness |
| # of images in series |
| Client properties (e.g., Client ID) |
| Connection (e.g., minimum bandwidth) |
| Site properties (e.g., site ID) |
| user properties (e.g., user ID and/or role) |
| Exam properties (e.g., exam type) |
| Temporal (e.g., day, time, etc.) |

FIG. 2

*User-Defined Rules*

| User Info | |
|---|---|
| User ID | JSMITH1221 |
| User Type | Radiologist |
| | |
| Thin Slice Definition | |
| Slice Thickness: | <1mm  or |
| # of images in series | >400 |
| | |
| Device | Home |
| Download | upon request |
| Include on Physical Media | No |
| Include in Print | No |
| Include in Upload | Ask |
| Display as part of series | No |
| Delete after | 2 months |
| Compression Type | Smallest file size |
| | |
| -Exceptions | |
| Image Type | CT |
| Download | All |
| Include on Physical Media | No |
| Include in Print | Yes |
| Include in Upload | Ask |
| Display as part of series | Only in volume rendering mode |
| Delete after | 2 months |
| Compression Type | Smallest file size |

| Device | Hospital |
|---|---|
| Download | All |
| Include on Physical Media | No |
| Include in Print | No |
| Include in Upload | Yes |
| Display as part of series | Yes |
| Delete after | Never |
| Compression Type | Lowest Loss |

← 320

*Site Rules*

| Site Info | | |
|---|---|---|
| Site ID | Hospital-A | |
| Site Type | Hospital | |
| | | |
| Thin Slice Definition | | User Override Allowed? |
| Slice Thickness: | <2mm | Yes |
| # of images in series | | |
| | | |
| Default Rules | | |
| Upload | All | Yes |
| Include on Physical Media | Yes | Yes |
| Include in Print | No | Yes |
| Display as part of series | Yes | Yes |
| Delete after | Never | No |
| Compression Type | Lowest Loss | Yes |
| | | |

FIG. 3C

RULES-BASED APPROACH TO RENDERING MEDICAL IMAGING DATA

CROSS-REFERENCE TO RELATED APPLICATIONS

This application is a continuation of patent application Ser. No. 12/891,543 filed on Sep. 27, 2010, titled "Rules-Based Approach to Transferring and/or Viewing Medical Images," which application claims the benefit of priority from U.S. Provisional Patent Application No. 61/246,479 filed on Sep. 28, 2009, titled "Rules-Based Approach to Transferring and/or Viewing Medical Images." The entire contents of each of the above identified applications is hereby incorporated by reference herein. All publications and patent applications mentioned in this specification are hereby incorporated by reference in their entirety to the same extent as if each individual publication or patent application was specifically and individually indicated to be incorporated by reference.

BACKGROUND OF THE INVENTION

1. Field of the Invention

This disclosure relates to transferring and/or viewing of medical images

2. Description of Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. Many imaging modalities are inherently digital, such as computed radiography (CR), digital radiography (DR), MRI (magnetic resonance imaging), CT (computed tomography), PET (positron emission tomography, NM (nuclear medicine scanning), FFDM (full-field digital mammography), and US (ultrasound), often yielding hundreds or even thousands of images per examination. Increasingly these digital images are viewed, manipulated, and interpreted using computers and related computer equipment. Accordingly, improved systems and methods are needed for distributing, viewing, and prioritizing these digital images under various network and viewing conditions.

SUMMARY

In one embodiment, a method of selecting medical images of an image series for transfer comprises, by a computing device executing software, performing operations comprising, accessing transfer criteria associated with a first computing device, the transfer criteria indicating thin slice criteria for determining whether respective medical images of an image series are classified as thin slices, wherein the thin slice criteria include at least one of a maximum thickness of a particular medical image for classification of the particular image as a thin slice image or a maximum quantity of medical images in the image series for classification of the medical images of the image series as thin slice images, selecting a first group of medical images of the image series that are thin slice images as indicated by the thin slice criteria, initiating transfer of the first group of medical images to the first computing device, wherein medical images of the image series that are not in the first group are not transferred to the first computing device.

In one embodiment, a method comprises, by a computing device comprising hardware, performing operations comprising accessing thin slice criteria for determining whether respective medical images of an image series are classified as thin slices, selecting a thin slice series of medical images that includes one or more medical images that are classified as thin slices based on the thin slice criteria, selecting a non-thin slice series of medical images that includes one or more medical images that are not thin slice images based on the thin slice criteria, and transferring or displaying the thin slice series in a different manner than the non-thin slice series, such that either the images of the thin slice series are selectively not transferred, selectively transferred with lower priority, selectively transferred but not displayed, or selectively transferred but otherwise displayed or processed in a selectively different manner.

In one embodiment, a tangible computer readable medium has instructions stored thereon, wherein the instructions are configured for reading by a computing device in order to cause the computing device to perform operations comprising accessing transfer criteria associated with a first computing device and a first user, the transfer criteria indicating thin slice criteria for determining whether respective medical images of an image series are classified as thin slice images, wherein the thin slice criteria include at least one of a maximum thickness of a particular medical image for classification of the particular image as a thin slice image or a maximum quantity of medical images in the image series for classification of the medical images of the image series as thin slice images, selecting a first group of medical images of an image series that are not thin slices as indicated by the thin slice criteria, and initiating transfer of the first group of medical images to the first viewing environment, wherein medical images of the image series that are not in the first group are not transferred to the first viewing environment.

In one embodiment, a method comprises by a computing device configured for displaying medical images, determining a storage location of a dataset, determining an availability of a processing server to process the dataset, in response to determining that the dataset is locally available to a processing server configured to process the dataset, requesting processing of the dataset by the processing server and accessing the processed dataset from the processing server, and in response to determining that the dataset is not locally available to the processing server and/or the processing server is not available to process the dataset, requesting transmission of at least some of the dataset to the computing device and processing the at least some of the dataset at the computing device.

BRIEF DESCRIPTION OF THE DRAWINGS

FIG. 2 illustrates a transfer criteria table including exemplary categories of properties/attributes on which rules may be based in establishing transfer criteria for a user, site, or other group of viewing devices.

FIGS. 3A, 3B, 3C illustrate example data structures having rules of varying types that may be included as part of transfer criteria.

DETAILED DESCRIPTION

Figure 1A:
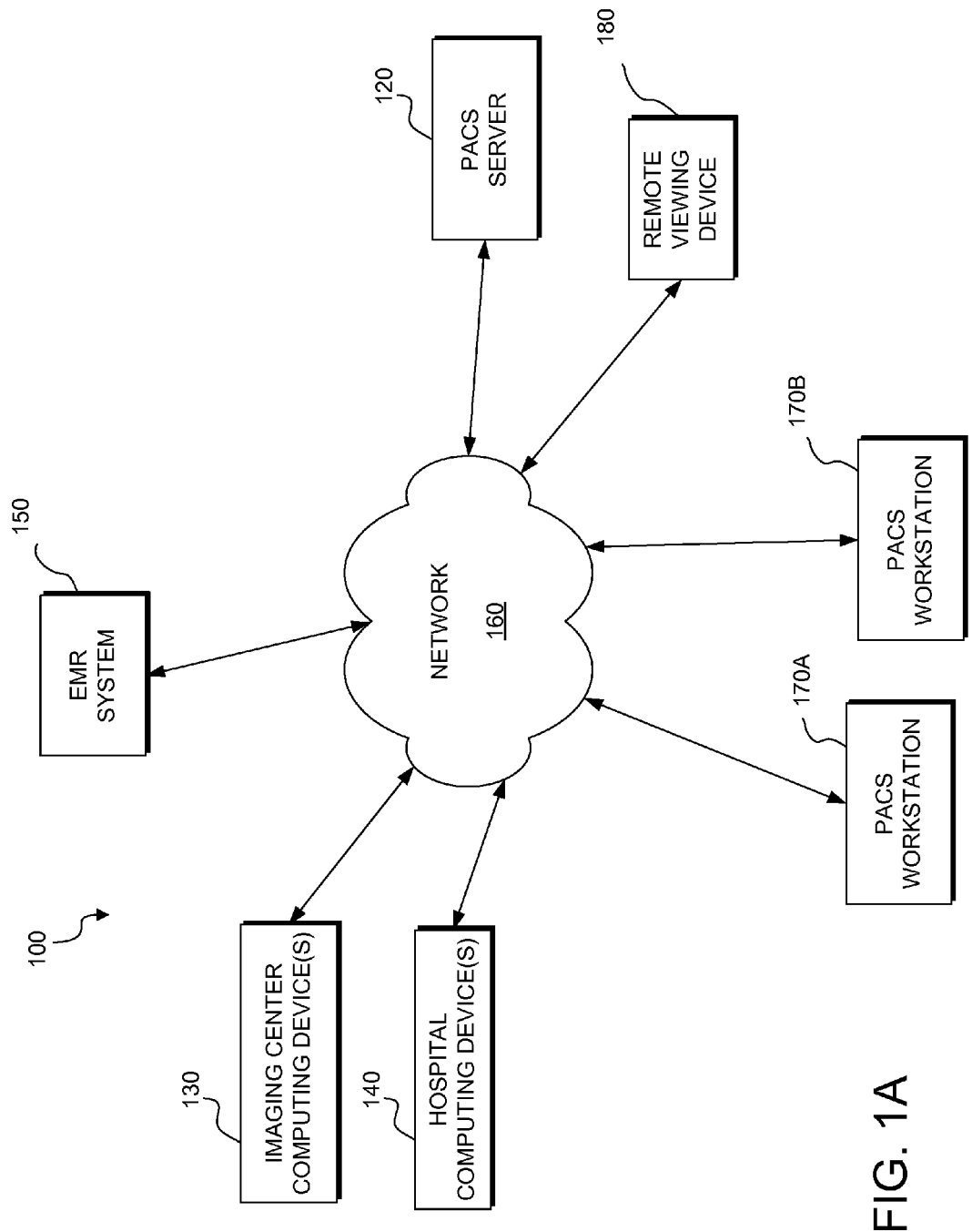
FIG. 1A is a block diagram of an exemplary medical imaging system including two PACS workstations in communication with various devices.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with certain specific embodiments. Furthermore, embodiments of the invention may include several novel features, no single one of which is solely responsible for its desirable attributes or which is essential to practicing the inventions herein described.

"Medical data," as used herein, is defined to include any data related to medical information, images, and/or other patient information. As non-limiting examples, medical data may include, but is not limited to, medical images, such as CR, DR, MRI, CT, US, PET, NM, FFDM and images related to gross and microscopic pathology, ophthalmology, endoscopy, or other medical images, as well as medical reports, such as text files containing reports, voice files with results summaries, and/or full digital dictation voice files for transcription. While this description is directed substantially to transmitting and viewing of medical images, the methods and systems described herein may also be used in conjunction with non-medical images, such as, images of circuit boards, airplane wings, and satellite images, for example.

"Thin slices," as used herein, generally refers to any medical images, or related images, having certain slice characteristics. For example, thin slices may be defined based on a number of slices, e.g., medical images, that are included in an image series. For example, thin slices might be defined to include images of any imaging series having more than 200 slices (or any other defined number of slices). Medical images may also, or alternatively, be defined based on a thickness of the cross section of the imaged tissue ("slice thickness") represented in the medical image. For example, thin slices might be defined to include images having a slice thickness of less than 1 mm (or any other defined slice thickness). The definition of thin slices may be adjusted based on one or more of many criteria, such as a particular user, site, imaging type, viewing environment (e.g., viewing device characteristic, bandwidth of viewing device) and any number of other related attributes. Thus, thin slices for a particular user at a first site may be defined differently than thin slices for another user at a second viewing site. Similarly, thin slices for a first modality or exam type may be defined differently than thin slices for a second modality or exam type. As described in further detail below, the definition of thin slices and how thin slices (as well as thick slices) are managed (e.g., transferred to various viewing devices) may vary in response to one or more of various attributes associated with the images.

In many medical imaging systems, thin slices, whether defined by a slice thickness and/or slice quantity, are typically stored in order to ensure that the thin slices are later available for use, if necessary. However, in many image viewing applications, some or all of the thin slices may not be necessary to download/view in order to allow the viewer to accurately read an image series. Thus, a viewing system, such as a PACS workstation, may download many thin slices, consuming valuable bandwidth and storage space, where the downloaded thin slices are never viewed by a viewer on the PACS workstation. On the other hand, certain thin slices, such as images associated with particular exam types or modalities, may need to be viewed in order to allow the viewer to accurately read an image series. For example, for certain exams thin slices may need to be reviewed in order to view details that cannot be appreciated in thick slices. Additionally, display environments, e.g., a combination of one or more of a display device, bandwidth, connection speed, availability of thin slices locally, etc., vary widely, such that some display environments might be better suited for viewing and/or downloading a greater quantity of thin slices, while other display environments might be better suited for having a server, such as the PACS server 120 of FIG. 1, render thin slices for viewing via a thin client interface with the display environment, while still other display environments may be better suited to not view or download thin slices at all, even via a thin client interface. Accordingly, the description below describes systems and methods that allow rules to be defined based on one or more of several attributes, such as a particular user, site, or device, as well as whether individual images and/or image series are classified as thin slices, and applied to medical images in order to determine which images are downloaded, viewed, stored, and/or any number of other actions that might be performed with respect to particular images.

Example Medical Imaging System

Figure 1B:
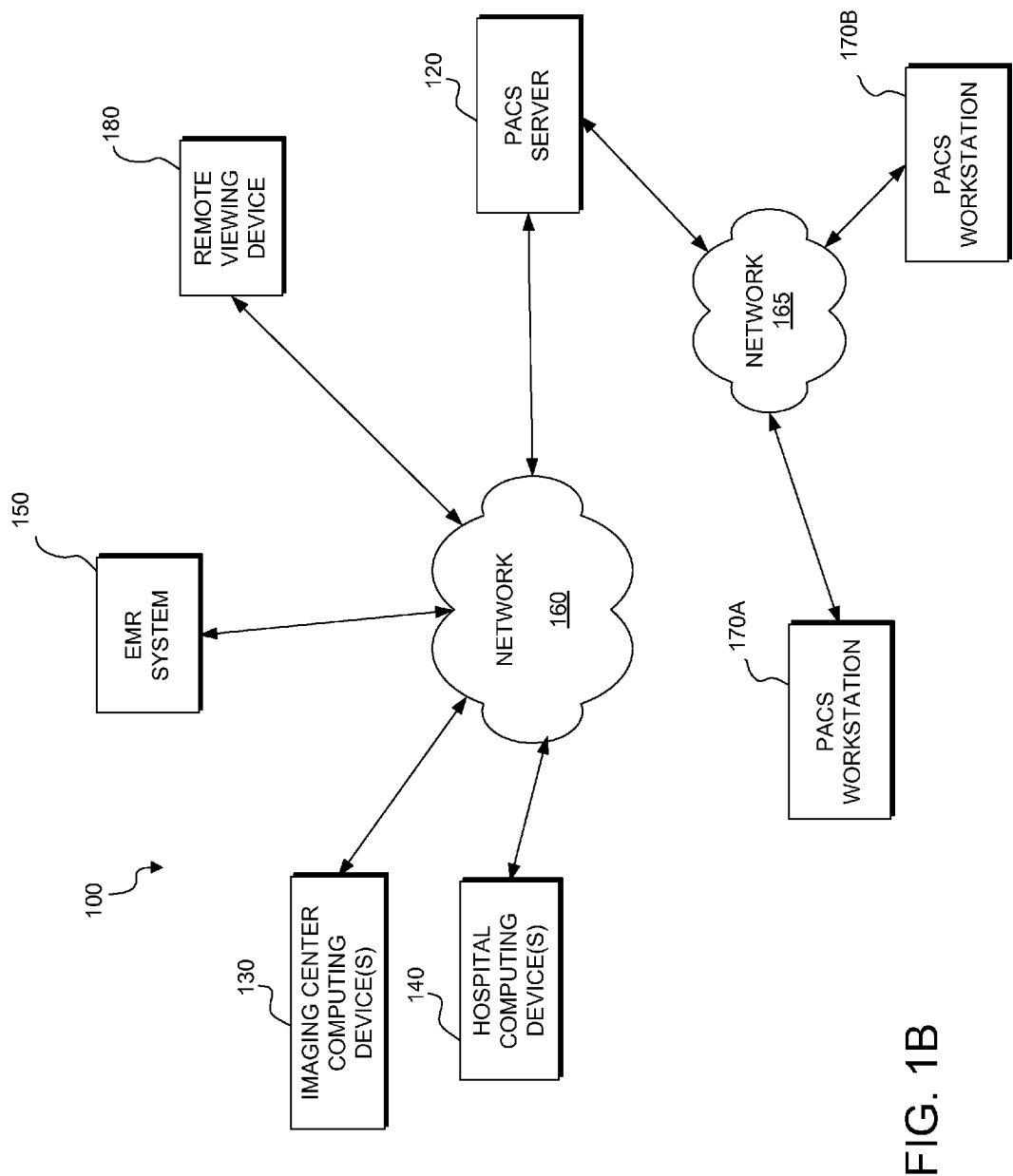
FIG. 1B is a block diagram of an exemplary medical imaging system wherein PACS workstations are in communication with a PACS server via a separate network which may comprise a secured local area network, for example.

FIG. 1A is a block diagram of an exemplary medical imaging system 100 including two PACS workstations 170A and 170B in communication with various devices. The PACS workstations 170A and 170B each include computing systems that are configured to view medical data, such as series of medical images. In the embodiment of FIG. 1A, the PACs workstations 170 and remote viewing device 180 receive medical data, including medical images, via a network 160, which may comprise one or more of any suitable network, such as local area networks (LAN), wide area networks (WAN), personal area networks (PAN), and/or the Internet, for example. In the embodiment of FIG. 1B, the PACS workstations 170 (which includes workstations 170A and 170B) are illustrated in communication with a PACS server 120 via a separate network 165 which may comprise a secured local area network, for example. In either embodiment, the viewing devices, such as the PACS workstations 170 and the remote viewing device 180, are configured to access, download, and/or view medical images. Depending on the embodiment, the viewing devices may each include a special-purpose computing device that is configured especially for viewing medical images or a general purpose computing device, such as a personal computer, that executes software for viewing medical images.

In the embodiment of FIGS. 1A and 1B, a number of entities/devices, including the imaging center computing device(s) 130, the hospital computing device(s) 140, and the EMR system 150 may generate and/or store medical data, including medical images of varying types, formats, etc., from various imaging devices. The imaging center computing device(s) 130 and the hospital computing device(s) 140 may each include multiple computing devices that are configured to generate, store, and/or transmit medical data, including medical images, to other computing devices, such as the EMR system 150, the PACs server 120, and/or any number of viewing devices, such as the PACs workstations 170 and/or remote viewing device 180.

In accordance with the systems and methods further described below, each of the viewing devices 170 and 180 may be configured to access, download, process and/or view thin slices in a different manner. For example, a user of the PACs workstation 170A may configure his workstation to not download any thin slices to the PACs workstation 170, where thin slices are defined as images representing a slice thickness of less than 1 mm, while the user of the PACs workstation 170B may also configure his workstation to not download any thin slices, but thin slices are defined as images of an image series having more than 200 images. Thus, each of the PACs workstations 170 may download and provide for viewing to viewers different images, such as different images that are classified as thin slices. Similarly, the remote viewing device 180, which is representative of a device that is not dedicated to viewing medical data, such as a home computing device of a doctor or radiologist, may define thin slices in a different manner, in consideration of bandwidth and hardware limitations, for example.

In addition to allowing medical image downloading, viewing, processing, and management to be based on their qualifications as thin slices, the systems and methods described herein allow rules for downloading, viewing, processing, storage and/or other management of thin slices, as well as other medical images and types of medical data, based on one or more of a plurality of attributes that are referred to herein as "transfer criteria." Thus, the transfer criteria, and the rules of the transfer criteria, may not only include rules regarding transfer of data (e.g., images, image series, exams, etc.), but may also include rules associated with viewing, processing, storing, printing, and/or otherwise manipulating or managing medical data, such as medical images. Transfer criteria related to transfer of data may be implemented in a push and/or pull architecture. For example, transfer criteria may be applied at a device that has local access to the image data for pushing of matching image data to a viewing device or transfer criteria may be applied at a viewing device for requesting (pulling) matching image data from the device that has local access to the image data.

Depending on the embodiment, transfer criteria may include criteria based on any attributes of images, series of images, exam descriptions, clinical indications, DICOM information, any other attribute, and/or any combination of attributes. For example, transfer criteria for transferring medical images to the PACs workstation 170A, may be based on not only whether medical images qualify as thin slices, the transfer criteria may be based on one or more of client (or viewing device) properties, connection properties, site properties, user properties, exam properties, and/or temporal properties, for example.

As noted above, transfer criteria may be based on image attributes, as well as series attributes. For example, transfer criteria may indicate that a first type of image should be transferred, but not a second type of image, even though the two image types might be within the same image series. As one example, in diffusion imaging of the brain, the user might want transfer of the isotropic diffusion images, but not the large number of anisotropic diffusion images that were used to create the isotropic diffusion images on the scanner. Thus, the user might want a rule indicating that anisotropic diffusion images of the brain are not transferred, burned on CD, or printed. Such a rule would not affect the transfer, burning, or printing of isotropic diffusion images, even where the isotropic diffusion images are included in the same image series as anisotropic diffusion images that are affected by the rule. Accordingly, transfer criteria indicating that isotropic diffusion images are transferred to a particular workstation, but that anisotropic diffusion images in the same series are not transferred to that workstation would not transfer any anisotropic diffusion images of an image series. The type of individual images may be determined in various manners, such as according to attributes in their respective DICOM headers.

Transfer criteria may also include series-based rules, such as to transfer image series of a particular modality while not transferring image series of other modalities. As another example of series-based transfer rules, consider a CT spine imaging series that includes two series, each 1,000 images × 0.5 mm, where the first series is reconstructed in bone algorithm for detection of fractures and the second series is reconstructed in soft tissue algorithm. The viewer might want to routinely transfer the image series in bone algorithm but not the image series in soft tissue algorithm. The two series may not be distinguishable by number of slices or slice thicknesses, but other information in the DICOM headers of the images in the series (e.g., series description or reconstruction algorithm) may be accessed to determine how and/or when the image series are transferred, viewed, processed, etc.

In another specific example of transfer criteria, images may be transferred based on series attributes as well as series description. For example, a brain CTA might include two large series, a large series of 0.6 mm images of the brain in bone algorithm before contrast and a large series of 0.6 mm images after contrast. The user might want the second images transferred routinely to evaluate the vessels, but not the first series. However, if the clinical history is "trauma" the user might elect to view the first series (bone algorithm) to evaluate for fractures. The two large series have similar slice thickness and image numbers but differ by other criteria, e.g., series description and administration of contrast.

As those of skill in the art will recognize, one reason to transfer certain images is for processing, such as 3D volumetric rendering or CAD (computer aided diagnosis), for example. While transfer criteria, as used herein, are discussed primarily with reference to transfers from a server, such as a PACS server 120 to a PACS workstation or other client machine, transfer criteria may also apply to transfer from a server to other machines, such as in response to viewing of an exam, or portions of the exam, on the PACS workstation. For example, when a viewer displays an exam, the transfer criteria might cause the thin slices to be transferred to a rendering server, and might involve transfer to more than one place. As a specific example, the rules for a particular viewer (or group of viewers) might be to transfer all image series to the viewer (e.g. to a remote viewing device at the viewer's home or office), including CTA source images that are categorized as thin slices, and to transfer the CTA source images to a 3D rendering server (because the remote viewing device may not be capable of 3D rendering). As another specific example, the rules for a particular viewer (or group of viewers) might be to transfer all image series to the viewer, except the CTA source images that are categorized as thin slices (because the remote viewing device is on a slow network connection), and to transfer the CTA source images to a 3D rendering server for both rendering of the images and viewing the source images in client-server mode.

Because transfer criteria may be based on such a large range of attributes, transfer criteria for each user may differ. Similarly, transfer criteria for combinations of a user with different sites may differ and transfer criteria for combinations of a user with different viewing devices may differ. Thus, in one embodiment transfer criteria comprise a set of rules that may vary from one combination of an image, user, site, viewing device, etc., to another combination of an image, user, site, viewing device, etc. Thus, systems and methods described herein provide flexibility in configuring a particular device, one or more devices at a particular site, any device operated by a particular user or class of user, etc., for downloading, viewing, and/or otherwise managing medical images, including thin slices.

The imaging center computing device(s) 130 may include one or more imaging devices of any type, such as imaging devices that are configured to generate MRI, x-ray, mammography, or CT images. In one embodiment, image data for certain medical images is stored in Digital Imaging and Communications in Medicine ("DICOM") format. The complete DICOM specifications may be found on the National Electrical Manufactures Association Website at <medical.nema.org>. Also, *NEMA PS 3—Digital Imaging and Communications in Medicine,* 2004 ed., Global Engineering Documents, Englewood Colo., 2004, provides an overview of the DICOM standard. Each of the above-cited references is hereby incorporated by reference in their entireties.

The exemplary PACS server 120 is configured to store images from multiple sources and in multiple formats, and may be configured to render certain medical images for display on one or more viewing devices via a thin network communication link, for example. For example, the PACS server 120 may be configured to receive medical images in the DICOM format from multiple sources, store these images, and selectively transmit medical images to requesting viewing devices.

The hospital computing device(s) 140 may include and/or be replaced with any other medical facility, such as clinic, doctor's office, or any other medical facility. These medical facilities may each include one or more imaging devices and may share medical images with the PACS server 120 or other authorized computing devices.

Example Display Environments

In one embodiment, each of the PACs workstations 170 and the remote viewing device 180 are configured to download, store, and display medical images. Thus, each of these devices is part of a respective display environment, where the display environment for each device may also include attributes such as a network connection speed, display device characteristics, allotted and/or available storage space, processing speed, and/or other attributes that may affect how medical data is downloaded, stored, and/or viewed by the devices. As used herein, the term viewing device refers to a computing system that is used in a display environment, where the viewing devices could include any type of device, such as a smart phone, a tablet computer, a notebook computer, a desktop computer, a server, any other computing device or combination of devices. Thus, each of the PACs workstations 170 and remote viewing device 180 include one or more viewing devices having associated display environments.

Each viewing device includes, for example, one or more computing devices and/or servers that are IBM, Macintosh, Windows, Linux/Unix, or other operating system compatible. In one embodiment, viewing devices each include one or more central processing units ("CPU"), such as conventional or proprietary microprocessors, and one or more application modules that comprise one or more various applications that may be executed by the CPU 105. The application modules may include software, firmware, hardware, or any combination thereof. Software application modules (or simply "software modules") configured for execution on computing devices may be provided on a computer readable medium, such as a compact disc, digital video disc, flash drive, or any other tangible medium. Such software code may be stored, partially or fully, on a memory device of the executing computing device for execution by the computing device. The application modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The viewing devices may further include one or more memories, such as random access memory ("RAM") for temporary storage of information and read only memory ("ROM") for permanent storage of information, and one or more mass storage devices, such as a hard drive, diskette, and/or optical media storage device. Typically, the components of the viewing device are connected to the computing device using a standards-based bus system. In different embodiments, the standards based bus system could be Peripheral Component Interconnect (PCI), Microchannel, SCSI, Industrial Standard Architecture (ISA) and Extended ISA (EISA) architectures, for example.

The viewing devices are generally controlled and coordinated by operating system software, such as the Windows 95, 98, NT, 2000, XP, 7 or other compatible operating systems. In Macintosh systems, the operating system may be any available operating system, such as MAC OS X. In other embodiments, the viewing device may be controlled by Linux/Unix or variants thereof, other open-source operating systems, or any other proprietary operating system. Conventional operating systems control and schedule computer processes for execution, perform memory management, provide file system, networking, and I/O services, and/or provide a user interface, such as a graphical user interface ("GUI"), among other things.

The viewing devices may include one or more of commonly available input/output (I/O) devices and interfaces, such as a keyboard, mouse, touchpad, and/or printer. In one embodiment, the I/O devices and interfaces for a viewing device may include one or more display devices, such as a monitor, that allows the visual presentation of data, such as medical images and/or other medical data, to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the viewing device or another device that is local or remote, displayed on a display device, and manipulated by one or more application modules. Viewing devices may also include one or more multimedia devices, such as speakers, video cards, graphics accelerators, and microphones, for example.

The viewing devices may include one or more communication interfaces that allow communications with various external devices. For example, the viewing devices of FIG. 1A are each interfaces to a network 160 that includes one or more of a LAN, WAN, or the Internet, for example. The network 160 may further interface with various computing devices and/or other electronic devices. In the exemplary embodiment of FIG. 1A, the network 160 is coupled to imaging center 130, a hospital 140, an EMR 150, and a PACS server 120, which may each include one or more computing devices. In addition to the devices that are illustrated in FIG. 1, the network 160 may communicate with other computing, imaging, and storage devices.

All computing devices described herein include different combinations of the components describes with reference to FIG. 1A, as well possibly additional components. For example, a server may include a processor with increased processing power, additional storage devices, but not all of the input/output devices.

The methods described and claimed herein may be performed by any suitable computing device, such as the viewing devices and/or computing devices of imaging centers, hospitals, EMR systems, PACS, and the like.

The methods may be executed on the computing devices in response to execution of software instructions or other executable code read from a tangible computer readable medium. A computer readable medium is a data storage device that can store data in a form that is readable by a computer system. Examples of computer readable mediums include read-only memory, random-access memory, other volatile or non-volatile memory devices, CD-ROMs, magnetic tape, flash drives, and optical data storage devices.

Rules-Based Approach to Image Display, Routing and/or Preloading

As noted above, various imaging devices generate medical images having a wide range of characteristics, such as slice thicknesses and slice quantities included in respective image series. Thus, medical images of various modalities, such as thin axial CT, MRI, PET, or other, may be transferred for display by one or more viewing devices. The medical images may include image series with thin slices, as well as thicker slices, such as thicker axial, coronal, and/or sagittal images, for example. In one embodiment, the thin slices may be stored for occasional use in the near or long term. One or more sets of rules that collectively comprise transfer criteria may de defined by individual users and/or administrators of entire sites, for example, to define what medical images should be classified as "thin slices," based on image slice thickness and/or the number of images in a series, for example. Depending on the embodiment, the transfer criteria, which may include thin rules, may be stored at any location(s), such as local to a remote viewing device, local to a PACS server, and/or at a network location that is accessible to both remote viewing devices and PACS servers, for example. The transfer criteria may be stored in any data structure, such as a database or XML file, for example, on any computer readable medium.

The transfer criteria may allow a user to indicate a preference as to whether thin slices are automatically displayed by default, or if thin slices are only displayed when requested by the user. For example, if an exam includes several image series, including one or more series having thin slices, a site may establish transfer criteria that control if and how these thin slices are downloaded and/or displayed. Additionally, the transfer criteria may allow individual users to assign rules that override the site rules. Thus, a first user at a particular display environment may be automatically presented with thin slices based on the transfer criteria, while a second user at the same display environment is only presented with the thin slices if a specific request to download/view the thin slices is made by the second user, in view of different user rules in the transfer criteria.

In one embodiment, rules of the transfer criteria may indicate whether thin slices are transmitted to remote sites, such as the remote viewing device 180 of FIG. 1, based on a variety of criteria, including preferences of the individual user, characteristics of the viewing environment, the user role, available bandwidth, the software client, or many others. For example, a rule might indicate that referring doctors are not presented with thin slices for display by default. Another rule might indicate that for certain users or sites, for example, when media such as a CD or DVD is created and/or when an exam is uploaded to a PHR or EMR, for example, the thins slices are not included. Another rule might indicate that when film is printed, the thin slices are not printed.

Rules may also indicate whether thin slices are preloaded into RAM while reading and/or may indicate the priority of preloading. For example, thin slices and/or an entire image series having thin slices might be preloaded into RAM when an exam is displayed, but the thin slices might not actually be displayed, but instead maintained in RAM for immediate access if the user decides to display the thin slice. Other alternatives for transferring, loading into memory, and/or displaying thin slices may also be specified in rules. For example, rules may indicate that (i) thin slices are to be loaded into RAM and displayed after (or while) downloading the images, (ii) the thin slices are loaded into the local memory of the viewing computer and not automatically pre-loaded into RAM or displayed until the user specifies, and/or (iii) thin slices are assigned a lowest priority for use of RAM, such that the thin slices are loaded into RAM only after the other non-thin images of an exam are loaded. Thus, transfer criteria may include rules that not only relate to movement of images between computing devices, but also within a device, such as whether images are pre-loaded into RAM, the priority of such loading, and whether they are displayed.

FIG. 2 illustrates a transfer criteria table including exemplary categories of properties/attributes on which rules may be based in establishing transfer criteria for a user, site, or other group of viewing devices. In the embodiment of FIG. 2, the first two listed properties are slice thickness and number of images in series. As noted above, medical images may be classified as thin slices based on one or both of these first two properties. In some embodiments, transfer criteria may include only rules used to categorize images as thin slices. However, as indicated in FIG. 2, for example, many other attributes associated with medical images and the viewing environment may be included in rules of transfer criteria, such that different viewing environments may not only define thin slices differently, but may interface with thin slices in different manners, based on other rules of the transfer criteria. In some embodiments, the transfer criteria may also be used as criteria for downloading, viewing, printing, storing, deleting, and/or otherwise managing medical data that match the indicated transfer criteria. Alternatively, separate sets of criteria, similar to the transfer criteria, may be established for downloading, viewing, and/or storing medical images, for example.

In the embodiment of FIG. 2, the properties include one or more client properties, such as a client ID that may identify a particular viewing device and/or viewing environment, for example. The client properties may include individual characteristics of a client, such as hardware and/or software capabilities of a particular viewing device. The connection properties may indicate various characteristics of a connection between a viewing device and the Internet, for example, such as a connection speed, type of Internet service, and/or Internet service provider. The site properties may include a site identifier that identifies a particular site, class of sites, or group of sites. The user properties may indicate a particular user, such as by a user ID, username, or the like, as well as a user role, user access rights, user preferences, etc.

In one embodiment, site rules may indicate a default definition for thin slices, as well as rules for how thin slices are downloaded, viewed, and/or otherwise used by viewing devices associated with the particular site. Similarly, user rules may indicate a user specific, or user group specific, definition for thin slices, as well as user rules for how thin slices are downloaded, viewed, and/or otherwise used by viewing devices which the user is controlling. Thus, in one embodiment the site rules and the user rules may differ and, accordingly, may be reconciled by either overriding conflicting rules with the site rules, the user rules, requesting further input from the user, or applying some other rules for reconciling the conflicting rules.

The data structure of FIG. 2 also indicates that rules might be based on exam properties and/or temporal characteristics. In one embodiment, rules associated with one or more exam properties, such as an exam type, imaging device, referring doctor, imaging center, etc., may be considered in determining whether images are transferred to certain viewing devices. Other rules might indicate that only thin slices having a particular type of compression are to be transferred or viewed by a particular user, client, and/or site, for example. Such rules may be used in a real-time manner by a PACS server, to select a compression type that matches a compression type indicated in a rule so that the corresponding thin slices may be transmitted to the associated viewing devices. Rules may also be based on one or more temporal properties, such as when certain images should be downloaded, viewed, etc., by particular viewing devices, users, sites, etc. For example, a user may define a temporal rule indicating that thin slices, defined by the user and/or site rules, for example, should be downloaded to the user's viewing device only after 7:00 PM on weeknights or on weekend days.

Rules associated with one or multiple of the properties indicated in FIG. 2, as well as other properties or attributes, may be considered in determining if, when, and/or how, medical images, such as thin slices, are transferred, presented for viewing, viewed, stored, printed, etc.

As an example of a combination of rules based on multiple attributes, a first viewer may set a user rules indicating a personal preference to have only thick sections of CT scans displayed as a routine while reading, but also wants the thin slices preloaded into RAM and displayed only if the viewer goes into MPR or volume rendering mode. The same user may also set rules indicating that for certain exam types, e.g., CTA's for example, the thin slices are presented for viewing as a default, overriding the user's general preference to have only thick sections of CT scans displayed as a default. The user may also establish rules associated with different sites, such that when the viewer is at home, the same CTA thin slices are not displayed. Such rules may also be defined in terms of connection properties, such that if the home viewing device does not meet a particular minimum access speed, the thin slices are not downloaded to the viewing device or the thin slices are downloaded to the viewing device in the background, or the thin slices are downloaded only at certain days of the week and/or times, for example. Thus, the user rules that comprise transfer criteria may include various attributes and may be combined in various manners to produce robust and precisely customizable rules for transferring, viewing, and managing medical images.

Example Rules

FIGS. 3A, 3B, 3C illustrate example data structures having rules of varying types that may be included as part of transfer criteria. As discussed above, transfer criteria may vary depending on many attributes of a medical image or image series, as well as the respective viewing device to which the medical image might be transferred. For example, transfer criteria for a particular medical image might classify the medical image as a thin slice based on site rules of a first viewing device, while the same medical image is classified as a thick slice based on site rules of a second viewing device. Accordingly, the eventual transfer, viewing, and/or management of the medical image (or lack thereof) by the first and second viewing devices may be quite different. While the data structures of FIGS. 3A, 3B, and 3C illustrate certain rules that may be included in transfer criteria, rules based on any other attributes may also be included in other systems. Likewise, transfer criteria may include fewer rules and/or types of rules than is illustrated in the data structures of FIG. 3. Additionally, the transfer criteria may include more specific criteria for a particular type of rule that is illustrated in FIG. 3. The example of FIG. 3 is not intended as limiting the scope of rules, transfer criteria, or properties on which transfer criteria may be based, but rather is provided as one example of such rules and transfer criteria.

FIGS. 3A and 3B illustrates a sample data structure including user-specific rules. In this embodiment, the user establishes different rules for each of two locations associated with the user (home and hospital). In particular, section 310 of the data structure of FIG. 3A includes rules that are specific to a viewing device at the user's home. The rules associated with the user's home also include exceptions for a particular image type, specifically, a CT image type in this embodiment. Thus, the user has established rules that define how images are classified as thin slices, and further has defined how the thin slices should be managed by the user's home viewing device, with a particular set of rules for only CT images. The user has also established rules in section 320 that are specific to a viewing device used by the user at a hospital location. Thus, the viewing devices of the user at the home and hospital locations may receive different sets of the same medical images.

FIG. 3C illustrates a sample data structure including site rules, such as those that are developed by an administrator of a particular medical imaging center, doctors office, hospital, or other site that views and/or receives medical images. In one embodiment, site rules may be used as default rules for all viewing systems and/or users at or associated with the site. In the embodiment of FIG. 3C, the site rules indicate which rules can be overridden by user rules such as those in FIGS. 3A and 3B. In other embodiments, the site rules may be configured to always override conflicting user rules or the site rules may be configured to always be overridden by user rules. In other embodiments, other rules are used for reconciling conflicting site rules and use rules. As also noted above, rules based on various other attributes may be established by users of the system, and similar reconciliation schemes or rules may be used to determine the proper transfer criteria for a given image or image series.

Reconciliation of Rules

Figure 4:
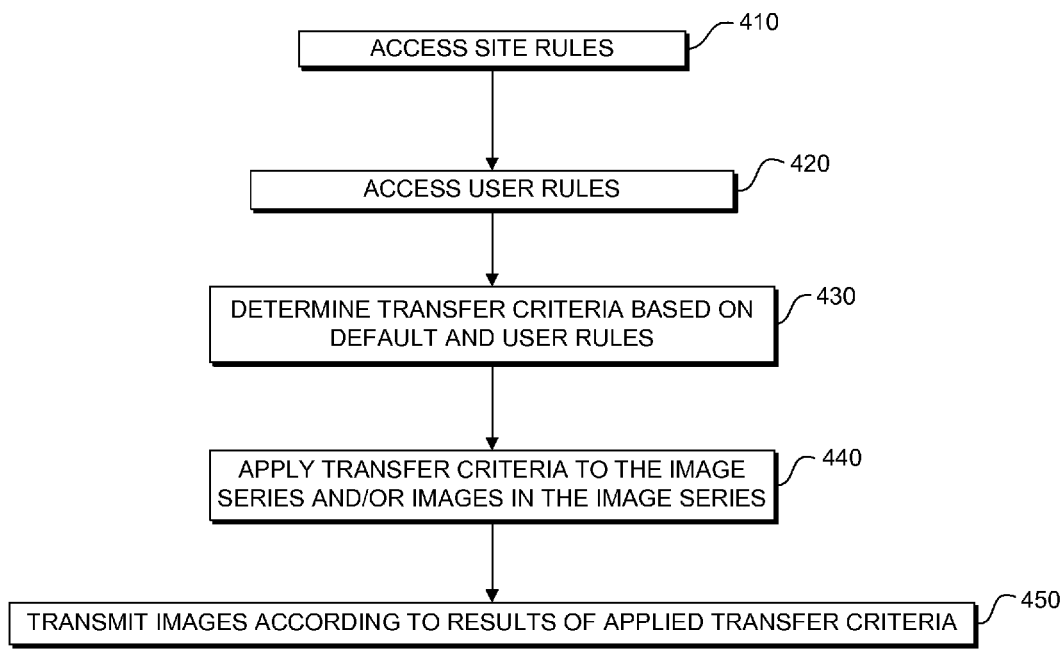
FIG. 4 is a flowchart illustrating one embodiment of a method of reconciling default, such as site rules, with user rules.

FIG. 4 is a flowchart illustrating one embodiment of a method of reconciling default, such as site rules, with user rules. A similar methodology may be performed in reconciling other types of rules, such as slice thickness definition rules, client specific rules, connection rules, exam rules, and temporal rules.

In one embodiment, various sets of rules, such as site rules and user rules, that are associated with a particular medical image or series of medical images, are reconciled in order to determine a set of transfer criteria associated with the particular medical image and viewing environment. Thus, the transfer criteria that are applied to a particular medical image may vary depending on rules associated with one or more of the viewing environment, the viewer, the site, the connection, and/or the client, for example. In one embodiment, the method of FIG. 4 is performed by a device that stores the medical images, such as the PACS server 120 or EMR system 150 of FIGS. 1A and 1B. Depending on embodiment, the method of FIG. 4 may include fewer or additional blocks and blocks may be performed in a different order than is illustrated. In addition, similar methods may be performed in order to determine whether medical images should be displayed, stored, printed, etc., based on the determined transfer criteria. Software code configured for execution on a computing device in order to perform the method of FIG. 4 may be provided on a computer readable medium, such as a compact disc, digital video disc, flash drive, or any other tangible medium. Such software code may be stored, partially or fully, on a memory device of the computing device in order to perform the method outlined in FIG. 4 by those respective devices.

Beginning at block 410, default rules, such as site rules, are accessed and in block 420 user rules are accessed. As indicated in FIGS. 3A, 3B, 3C, site rules and user rules may differ in both defining what medical images should be classified as thin slices and in determining how thin slices and/or thick slices should be treated in view of multiple possible attributes. In block 430, transfer criteria based on the default and user rules are determined. As noted above, the default and/or user rules may include rules defining required or excluded properties of many types, such as properties of the viewing environment, the viewer, the sights, the connection, the exam, and/or the client, for example. The computing device that performs the method of FIG. 4 reconciles the various default rules and user rules in order to determine transfer criteria for a particular image or image series. Next, in block 440, the determined transfer criteria are applied to the image and/or image series in order to determine how the images should be transferred, viewed, and/or stored, if at all, by the viewing device (e.g., a viewing device that is scheduled to receive the particular image series or a viewing device that requests image series). Finally, in block 450, medical images, such as thin and thick slices that meet the transfer criteria, are transferred to the viewing device.

Smart Switching

In certain medical imaging systems, one or both of user-side and server side applications operate upon a similar dataset of information, such as a dataset representing a series of medical images encompassing a volume of tissue. Such applications may be configured to render medical images from the dataset, for example, such as by using advanced processing of cross-sectional medical image series. However, if only a rendering server-side approach is used, the server typically stores a large number of medical data, including datasets associated with medical images, because the server cannot anticipate what medical data will require such advanced processing. Thus, the costs for such server-side systems may be high. In addition, various simultaneous users may compete for server availability and if the server goes down or becomes unavailable, all users may be adversely affected. Alternatively, if a pure client side approach is employed, when a user needs to process a series of images, the images must first be loaded into the memory of their viewing device (client), which often involves transmission of the datasets to the client from a storing server, which may cause a delay of several seconds to several minutes or more as the dataset is made available to the client application. In addition, a pure client-side approach requires that the application be loaded and maintained on each client.

In one embodiment, certain viewing devices and/or image serving devices, such as a PACS server or EMR system, execute a smart switching software module. A smart switching application may include a client-based software application capable of processing data (in this case, rendering of CT, MRI, PET, Ultrasound, for example, as multiplanar or volume rendered images) and optionally a server-based software application with that capability residing on the same network (e.g., network 160 and/or 165 of FIG. 1A, 1B). In one embodiment, the smart switching module on a viewing device is configured to detect the location of a desired dataset and, if the dataset is available on the rendering server, the processing operation(s) (e.g., rendering of the medical images) occurs there, and the results may be viewed on the viewing device via a thin-client viewer, for example. In this embodiment, if the dataset is not available on the rendering server, the rendering server is not available, is busy, and/or there is no rendering server, the dataset may be processed on (possibly after transmission to) the client-based smart switching module on the viewing device. In one embodiment, smart switching may be performed in response to application of smart switching rules that are based on any attributes, such as any one or more of the properties listed in FIG. 3, for example. In one embodiment, smart switching rules may include attributes related to a particular user (or group of users) or site (or group of sites), such that smart switching might be performed differently based on the current user and/or site, for example. Depending on the embodiment, the smart switching rules may be part of the transfer criteria or may be a separate rule set.

In some embodiments, a user and/or viewing device may want selected image series transferred to a rendering server as opposed to (or in addition to) transfer to a viewing device. For example, a viewer may want to do side-by-side volume rendering of a patient's abdominal aortic aneurysm by comparing the current exam to one from 2 years ago, but the thin slices from the old exam are not in the cache of the rendering server. Thus, the smart switching rules may indicate that the images from the 2 year old exam are transferred from a PACS server (that still stores the images) to a rendering server. Similarly, transfer criteria might specify that thin slices are not transferred to a viewing device, but instead might specify that the series be transferred to a central rendering server for 3D processing. Any other set of transfer criteria may be used to control transfer of images to a rendering server, one or more viewing devices, and/or other devices. For example, in the case of computer aided diagnosis (CAD), e.g. chest CT for nodules or breast imaging, transfer criteria might specify that the images be transferred to a processing server (in this case for CAD) as well as the viewing device for viewing.

As an example, consider a CT examination that contains 4 series: one axial series with two hundred 4 mm thick slices, one coronal series with one hundred 3 mm thick slices, one sagittal series with one hundred 3 mm thick sections, and one axial series with sixteen hundred 0.5 mm thick sections. Using an exemplary set of rules for defining thin slices, the axial series may be defined by the individual user or site as "thin" because of a slice thickness criteria of under 1 mm, or because of a image per series rule of >200 images.

As noted above, transfer criteria may indicate a user's preference to not display the thin series when images are typically viewed for reading, or not display them under only certain reading circumstances such as when the client is running with a slow network connection. Suppose the user is working on a client that has not downloaded the thin slices and decides to perform additional image processing while viewing the exam (e.g., perhaps the user wishes to create oblique slices or volume-rendered images). When the user accesses a tool for such advanced processing, e.g., included in the client smart switching module, the system recognizes that the thin slices are not present locally, determines that the thin slices are on a connected rendering server, and enables the user to access the advanced processing application on the server via a thin client (or other connection type), with the rendering operations performed on the server side. Alternatively, if the smart switching application determines that there is no server-side rendering engine available, the smart switching module determines that the thin slices are available but will need to be downloaded, and may initiate download (and possibly background downloading) of the thin slices. Suppose now that the user is working on a client that has downloaded the thin slices into local memory, and decides to perform additional image processing on the thin slices. The smart switching modules may be configured to determine if there is a networked rendering server with a copy of the thin slices, and if so, initiate the processing operations on the server side immediately, with display on the client via a thin client viewer and, if there is no rendering server, make the locally downloaded thin slices available to the locally resident processing application instead.

Use of one or more smart switching modules may advantageously load-balance activities of clients and servers in a way that can be user defined and based on real-time availability of one or more servers, for example. Such load balancing may allow the rendering server to store fewer exams, while allowing for decreased processing times to process data sets that might normally be processed by a client when the server is available for processing. As noted above, a smart switching system for advanced image processing may be combined with rules of varying types, including rules for defining thin slices. In one embodiment, a smart switching module supports the following workflow: (1) if a rule is set (e.g., a user, site, device, or other rule) to show no thin slices, the thin slices are not displayed under the indicated rule preferences (e.g., site rules may indicate that thin slices are not to be downloaded or viewed at a home location), and only the thick slice images are presented; (2) if a user wants to have an exam automatically loaded in advanced visualization mode (or otherwise processed) by rule or switch to that mode, and the thin slices are available on the rendering server, the thin slices can be rendered by the rendering server with minimal delay (as compared to the delay in rendering that might be experienced if rendered on the client); and/or (3) if a user wants to have an exam automatically loaded in advanced visualization mode by rule or switch to that mode, but the images are not available on any rendering server (e.g., the rendering server(s) are busy, down, not available, or absent entirely), the local client is used to render the thin slices, such as by making the appropriate dataset available to the client processing application in background so that other work can be performed in the meantime.

Rendering Server Cluster or Grid

In some embodiments, a rendering server may comprise a cluster or grid of computing devices. For example, a rendering server may include many computing devices that could serve as rendering servers, dedicated rendering servers, and/or other computing devices that can also serve as a rendering server, such as PACS workstation that renders images in a background process for other viewing devices.

For server side rendering, images may or may not be stored at each rendering device (where there are multiple possible rendering devices). For example, if there are multiple rendering devices capable of serving as a rendering server, it may not be efficient for each of them to have a copy of all the cases that might be subjected to rendering. Rendering may include any type of image generation or modification, such as 3D image rendering, 2D image rendering, adjusting a bit depth of images (e.g., adjusting 12-bit DICOM images into 8-bit JPEG images so they can be displayed in browsers and other light clients), and/or any other image manipulations. For ease of explanation, 3D rendering is discussed herein; however, any discussion of 3D rendering should be construed to also describe any other type of rendering.

In addition to each rendering device not having a copy of all image data, users may desire to render old exams that are not stored by any rendering device, for example to compare to new exams. In both cases, the images to be rendered may be transferred to the rendering device at the time of rendering. In one embodiment, a viewing device queries the group of rendering devices, or a device that load-balances rendering requests, with a request that the "fastest" rendering server provide processing. The "fastest" server might not be the fastest rendering device or least busy rendering device, but the one with the most rapid access to the data. For example, consider a series of imaging centers connected with a WAN, each with its own PACS server and 3D rendering device (could be the same machine). A user at site A might need to perform interactive 3D rendering of an exam at remote site B. While equivalent 3D rendering devices might exist at both site A and site B, the system may utilize the remote rendering server at site B because it has the fastest connection to the data, as the data resides locally at site B. Similarly, if images are stored at one rendering device, but not at others, the system may select the rendering device that already has a copy of the images for rendering, rather than another rendering device that might otherwise be used for the rendering In one embodiment, rendering of multiple exams requested by a particular viewer/viewing device might occur on different rendering devices. For example, a viewer may need to render a current exam and an old exam, such as to compare the images of the exams. If the old exam was performed at a hospital and the new exam at an imaging center, where it is also being read, the viewer at the imaging center needs to perform 3D volumetric rendering of the two exams, to assess for growth of an abdominal aortic aneurysm, for example. Rather than requiring rendering of both the current and old exams on a particular rendering device (e.g., at the imaging center), according to the systems and methods described herein, rendering of the old exam might be performed by a first rendering device (e.g., at the hospital where the exam is stored), while the new exam is rendered by a second rendering devices (e.g., a client machine at the imaging center).

Figure 5:
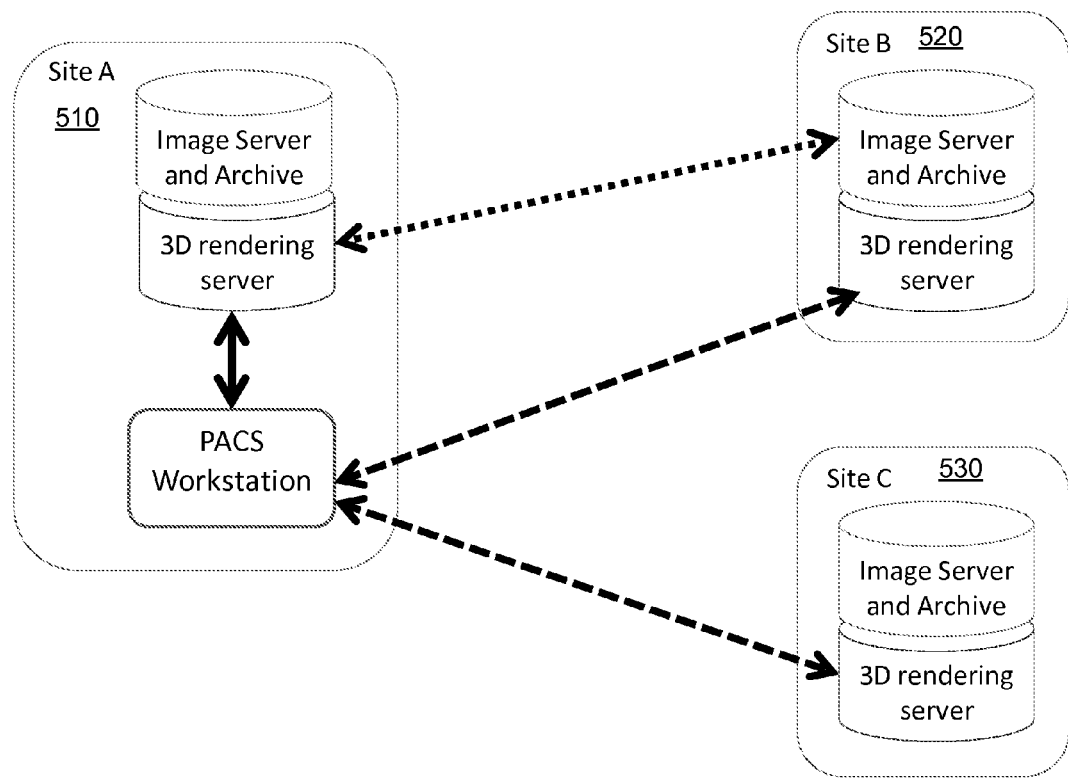
FIG. 5 is a block diagram of three sites that are configured to perform one or more of the operations discussed herein.

FIG. 5 is a block diagram of three sites that are configured to perform one or more of the operations noted above. In particular, FIG. 5 illustrates that site A 510 includes an image server and archive, a 3D rendering server, and a PACS workstation, while each of Sites B 520 and C 530 also include an image server and archive and a 3D rendering server. In one embodiment, the PACS workstation at site A 510 is operated by a viewer (e.g., radiologist or doctor) in order to view medical images that are rendered by any of the site A, B, or C rendering servers. In other embodiments, the PACS workstation at site A may be replaced by any other viewing device, such as a desktop computer configured to access medical images via a browser or other software, a smart phone, a tablet computer, and/or laptop computer.

In the embodiment of FIG. 5, Site A has requested rendered images that include thin slice images (e.g., either in response to rules that initiate automatic rendering/transfer of the images and/or a request for the rendered images from a user of the PACS workstation at site A 510, for example). However, rather than transferring the large set of thin slice image data from the image server at Site B 520 for rendering by the local rendering server at Site A 510, the workstation A utilizes the rendering server at Site B 520, which has fast local access to the thin slice image data. Thus, processing power at Site A 510 may be used for other purposes while Site B 520 renders the images. Alternatively, if the thin slice image data is stored local to Site A 510, the 3D images may be rendered locally at Site A 510. As discussed above, the rules for defining which device should perform rendering may be based on any number of factors.

In another example, there might be exams that a user at Site A 510 wants to render that are at remote sites B and C, which are connected via slow networks. Thus, one option is to have the exams transferred from these remote sites to the local 3D rendering server at Cite A 510. However, transfer of the image data might be slow. Alternatively, using the smart switching methods described above, the rendering servers at Sites B 520 and Sites C 530 may be automatically utilized to render the images at those remote sites. In one embodiment, such remote rendering may be selected in response to rules, such as a rule that automatically initiates remote rendering of image data for images that are defined as thin slice images and/or based on the bandwidth between the remote rendering servers (e.g., at sites B 520 and C 530).

In one embodiment, images may be rendered at multiple remote rendering devices (e.g., rendering servers at Sites B 520 and C 530) for viewing at a workstation (e.g., PACS workstation at Site A 510). For example, if image data for a first exam of a patient is locally accessible to Site B 520 and image data for a second exam of the patient is locally accessible to Site C 530, and a user of the workstation at Site A 510 wishes to compare rendered images from the first and second exams, images may be rendered by each of the rendering servers at Sites B 520 and C 530 using the respective locally available image data so that Site A 520 may not need to do any image rendering in order to view rendered images of two exams that have been rendered by different remote rendering servers.

Advantageously, distribution of rendering tasks in the manners discussed above may be performed based on rules that initiate rendering by local and/or remote rendering devices, such that the user does not need to manually coordinate rendering of various image data.

The foregoing description details certain embodiments of the invention. It will be appreciated, however, that no matter how detailed the foregoing appears in text, the invention can be practiced in many ways. For example, the above-described auto-retrieve may be performed on other types of images, in addition to medical images. For example, images of circuit boards, airplane wings, and satellite imagery may be analyzed using the described systems, in addition to medical images. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method comprising:
by a computing device configured for displaying medical images:
determining that a dataset is stored at a first storage location remote from the computing device;
determining an availability of a first processing server local to the first storage location to render the dataset, the first processing server configured to render the dataset;
in response to determining that the first processing server is available to render the dataset, requesting rendering of the dataset by the first processing server and accessing the rendered dataset from the first processing server; and
in response to determining that the first processing server is not available to render the dataset, requesting transmission of at least some of the dataset to the computing device and rendering the at least some of the dataset at the computing device,
wherein rendering comprises generating at least one of a 2D image or 3D image from the dataset.

2. The method of claim 1, wherein the dataset comprises 3D volumetric medical imaging data.

3. The method of claim 1, wherein the first processing server comprises a server configured to render 3D volumetric medical imaging data.

4. The method of claim 1, wherein accessing the rendered dataset from the processing server comprises displaying the at least one of a 2D image or 3D image rendered from the dataset rendered by the first processing server via a thin client interface with the first processing server.

5. The method of claim 1, wherein the at least some of the dataset comprises a portion of the dataset selected based on one or more characteristics of the computing device.

6. The method of claim 1 further comprising:
by the computing device configured for displaying medical images:
prior to rendering the dataset at either the first processing server or the computing device, determining if the dataset was previously rendered and is stored at another location and, in response to determining that the dataset was previously rendered and is stored at another location, requesting access and/or transfer of the dataset that was previously rendered.

7. The method of claim 1 further comprising:
by the computing device configured for displaying medical images:
querying a group of processing servers or a device that load-balances the group of processing servers with a request that a best available processing server of the group of processing servers is selected for rendering the dataset.

8. The method of claim 7, wherein the best available processing server is not a fastest processing server of the group of processing servers but is the processing server with the most rapid access to the dataset.

9. The method of claim 1 further comprising:
by the computing device configured for displaying medical images:
accessing smart switching rules that indicate criteria for determining whether respective datasets are rendered by the computing device or one or more processing servers.

10. A computer system comprising:
one or more computing devices configured for executing software instructions; and
a non-transitory computer-readable medium in communication with the one or more computing devices and having software instructions stored thereon, the software instructions configured for reading by the one or more computing devices in order to perform operations comprising:
determining that a medical imaging dataset is stored at a storage location remote from the computer system;
in response to determining that the rendering server is available to render the medical imaging dataset, requesting rendering of the medical imaging dataset by the rendering server and accessing the rendered medical imaging dataset from the rendering server; and
in response to determining that the rendering server is not available to render the medical imaging dataset, requesting transmission of at least some of the medical imaging dataset to the computer system and rendering the at least some of the medical imaging dataset at the computer system, wherein rendering comprises generating at least one of a 2D image or 3D image from the medical imaging dataset.

11. The computer system of claim 10, wherein accessing the rendered medical imaging dataset from the rendering server comprises displaying the at least one of a 2D image or 3D image rendered from the medical imaging dataset by the rendering server via a thin client interface in communication with the rendering server.

12. The computer system of claim 10, wherein the at least some of the medical imaging dataset comprises a portion of the medical imaging dataset selected based on one or more characteristics of the computer system.

13. The computer system of claim 10, the software instructions further configured for reading by the one or more computing devices in order to perform operations comprising:
  prior to rendering the medical imaging dataset at either the rendering server or the computer system, in response to determining that the medical imaging dataset was previously rendered and is stored at another location, requesting access and/or transfer of the medical imaging dataset that was previously rendered from the another location.

14. The computer system of claim 10, the software instructions further configured for reading by the one or more computing devices in order to perform operations comprising:
  querying a group of rendering servers or a device that load-balances the group of rendering servers with a request that a best available rending server of the group of rendering servers is selected for rendering the medical imaging dataset.

15. The computer system of claim 14, wherein the best available rending server is not a fastest rending server of the group of rendering servers but is the rendering server with the most rapid access to the medical imaging dataset.

16. The computer system of claim 10, the software instructions further configured for reading by the one or more computing devices in order to perform operations comprising:
  accessing smart switching rules that indicate criteria for determining whether respective medical imaging datasets are rendered by the computer system or one or more rendering servers.

17. A non-transitory computer-readable medium having instructions stored thereon, the instructions configured for reading by a computing device in order to perform operations comprising:
  determining that a dataset is stored at a storage location remote from the computing device;
  in response to determining that the processing server is available to render the dataset, requesting rendering of the dataset by the processing server and accessing the rendered dataset from the processing server; and
  in response to determining that the processing server is not available to render the dataset, requesting transmission of at least some of the dataset to the computing device and rendering the at least some of the dataset at the computing device,
  wherein rendering comprises generating at least one of a 2D image or 3D image from the dataset.

18. The non-transitory computer-readable medium of claim 17, wherein the dataset comprises medical imaging data, and wherein the at least some of the dataset comprises a portion of the dataset selected based on one or more characteristics of the computing device.

19. The non-transitory computer-readable medium of claim 17, wherein the instructions are further configured for reading by the computing device in order to perform operations comprising:
  prior to rendering the dataset at either the processing server or the computing device, in response to determining that the dataset was previously rendered and is stored at another location, requesting access and/or transfer of the dataset that was previously rendered.

20. The non-transitory computer-readable medium of claim 17, wherein the instructions are further configured for reading by the computing device in order to perform operations comprising:
  querying a group of processing servers or a device that load-balances the group of processing servers with a request that a best available processing server of the group of processing servers is selected for rendering the dataset.

21. The non-transitory computer-readable medium of claim 17, wherein the best available processing server is not a fastest processing server of the group of processing servers but is the processing server with the most rapid access to the dataset.

22. A method comprising:
  by a computing device configured for displaying medical images:
    receiving a request for least one of a 2D image or 3D image from each of a first dataset and a second dataset, the first dataset comprising an exam of a patient obtained at a first time, the second dataset comprising an exam of the patient obtained at a second time;
    determining that the first dataset is stored at a first storage location remote from the computing device;
    determining that the second dataset is stored at a second storage location remote from the computing device, the second storage location being different from the first storage location;
    determining an availability of a first processing server local to the first storage location to render the first dataset, the first processing server configured to render the first dataset;
    determining an availability of a second processing server local to the second storage location to render the second dataset, the second processing server configured to render the second dataset;
    in response to determining that both the first processing server and the second processing server are available to render the respective first and second datasets, requesting rendering of the first and second datasets by the respective first and second processing servers and requesting transmission of the rendered first and second datasets from the respective first and second processing servers to the computing device;
    in response to determining that the first processing server is not available to render the first dataset, requesting transmission of the first dataset to the computing device and rendering the first dataset at the computing device; and
    in response to determining that the second processing server is not available to render the second dataset, requesting transmission of the second dataset to the computing device and rendering the second dataset at the computing device, wherein rendering comprises generating at least one of a 2D image or 3D image from a dataset.

* * * * *